(12) United States Patent
Colgan et al.

(10) Patent No.: US 6,264,689 B1
(45) Date of Patent: Jul. 24, 2001

(54) LOW PROFILE MEDICAL STENT

(75) Inventors: Darragh Colgan, Galway (IE); Peter Hamilton, East Bridgewater; Paul DiCarlo, Middleboro, both of MA (US)

(73) Assignee: SciMed Life Systems, Incorporated, Maple Grove, MN (US)

( * ) Notice: Subject to any disclaimer, the term of this patent is extended or adjusted under 35 U.S.C. 154(b) by 0 days.

(21) Appl. No.: 09/052,214

(22) Filed: Mar. 31, 1998

(51) Int. Cl.$^7$ .................................................. A61F 2/00
(52) U.S. Cl. ................................................... 623/1.22
(58) Field of Search ................................. 623/1, 11, 12, 623/1.15–1.22

(56) References Cited

U.S. PATENT DOCUMENTS

| | | | |
|---|---|---|---|
| 3,868,956 | 3/1975 | Alfidi et al. | 128/345 |
| 4,776,337 | 10/1988 | Palmaz | 128/343 |
| 4,990,151 | 2/1991 | Wallstén | 606/108 |
| 4,994,071 * | 2/1991 | MacGregor | 606/194 |
| 5,015,253 | 5/1991 | MacGregor | 623/1 |
| 5,019,090 | 5/1991 | Pinchuk | 606/194 |
| 5,026,377 | 6/1991 | Burton et al. | 606/108 |
| 5,061,275 | 10/1991 | Wallstén et al. | 623/1 |
| 5,064,435 | 11/1991 | Porter | 623/12 |
| 5,133,732 * | 7/1992 | Wiktor | 606/195 |
| 5,159,920 | 11/1992 | Condon et al. | 128/6 |
| 5,171,262 | 12/1992 | MacGregor | 623/1 |
| 5,201,901 | 4/1993 | Harada et al. | 606/198 |
| 5,211,658 | 5/1993 | Clouse | 623/1 |
| 5,256,158 | 10/1993 | Tolkoff et al. | 604/280 |
| 5,282,823 | 2/1994 | Schwartz et al. | 606/198 |
| 5,304,220 | 4/1994 | Maginot | 623/1 |
| 5,366,504 * | 11/1994 | Anderson | 623/1 |
| 5,382,259 | 1/1995 | Phelps et al. | 606/151 |
| 5,405,377 | 4/1995 | Cragg | 623/1 |
| 5,405,378 | 4/1995 | Strecker | 623/1 |
| 5,411,507 | 5/1995 | Heckele | 606/108 |
| 5,484,444 | 1/1996 | Braunschweiler et al. | 606/108 |
| 5,534,007 | 7/1996 | St. Germain et al. | 606/108 |
| 5,534,287 | 7/1996 | Lukic | 427/2.25 |
| 5,571,167 | 11/1996 | Maginot | 623/1 |
| 5,603,698 | 2/1997 | Roberts et al. | 604/104 |
| 5,607,466 | 3/1997 | Imbert et al. | 623/1 |
| 5,643,339 * | 7/1997 | Kavteldze | 623/1 |
| 5,645,559 | 7/1997 | Hachtman et al. | 606/198 |
| 5,653,727 | 8/1997 | Wiktor | 606/195 |
| 5,667,523 * | 9/1997 | Bynon | 606/198 |
| 5,725,571 | 3/1998 | Imbert et al. | 623/1 |
| 5,725,572 * | 3/1998 | Cam | 606/191 |
| 5,728,150 | 3/1998 | McDonald et al. | 623/1 |
| 5,728,158 | 3/1998 | Lau et al. | 623/12 |
| 5,800,519 * | 9/1998 | Sandock | 623/1 |
| 5,843,168 * | 12/1998 | Dang | 623/1 |
| 5,876,432 * | 3/1999 | Lau | 623/1 |
| 5,928,280 | 7/1999 | Hansen et al. | 623/1 |

FOREIGN PATENT DOCUMENTS

| | | |
|---|---|---|
| 0 744 163 A1 | 11/1996 | (EP) . |
| 0 788 012 A2/A3 | 6/1997 | (EP) . |
| 0 788 802 A2 | 8/1997 | (EP) . |
| 0 804 934 A2 | 11/1997 | (EP) . |
| 0 812 579 A1 | 12/1997 | (EP) . |
| 894 505 A2 | 2/1999 | (EP) . |
| 87/04935 | 8/1987 | (WO) . |
| 94/00178 | 1/1994 | (WO) . |
| 95/29646 | 11/1995 | (WO) . |
| 96/32078 | 10/1996 | (WO) . |
| 96/33677 | 10/1996 | (WO) . |
| 96/41589 | 12/1996 | (WO) . |
| 97/32456 | 9/1997 | (WO) . |

* cited by examiner

Primary Examiner—Michael J. Milano
(74) Attorney, Agent, or Firm—Hamilton, Brook, Smith & Reynolds, P.C.

(57) ABSTRACT

The invention relates to an implantable medical stent having a low profile for delivery through smaller lumens. The stent is constrained during delivery where the helically wrapped points of a diamond cell structure also include at least one crossed joint of intersecting strands to provide a reduced diameter.

23 Claims, 16 Drawing Sheets

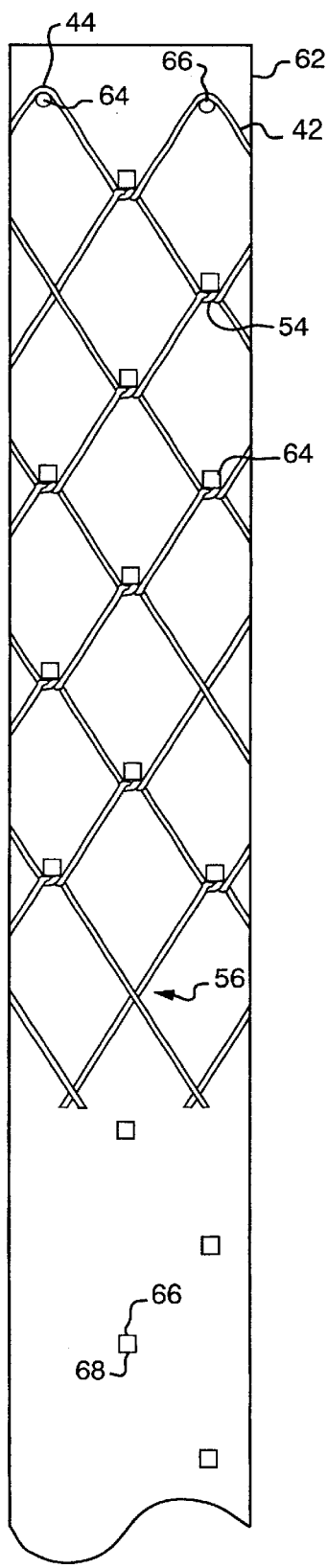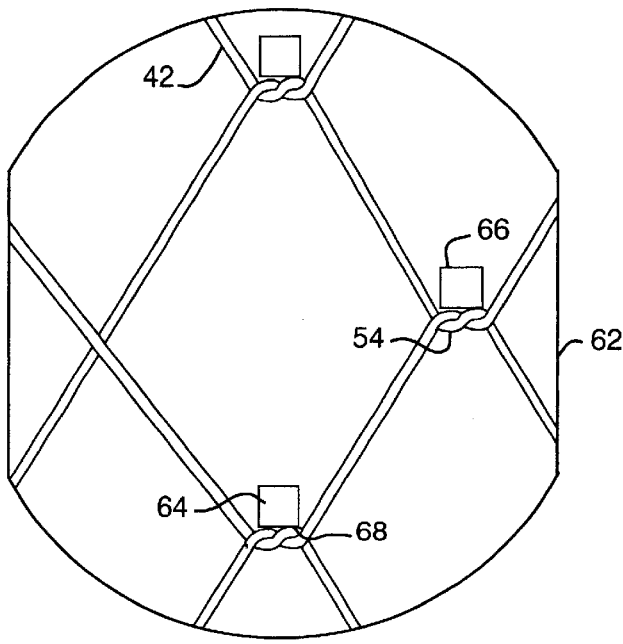
FIG. 4A
FIG. 4B

LOW PROFILE MEDICAL STENT

BACKGROUND OF THE INVENTION

Implantable medical prostheses, such as stents, are placed within the body to maintain and/or treat a body lumen that has been impaired or occluded, for example, by a tumor. The stent can be formed of strands of material formed into a tube and are usually delivered into the body lumen using a catheter. The catheter carries the stent to the desired site and the stent is released from the catheter and expands to engage the inner surface of the lumen.

A self-expanding stent can be made of elastic materials. These are held in a compressed condition during catheter delivery by, for example, a sheath that covers the compressed stent. Upon reaching the desired site, the sheath constraining the stent is pulled proximally, while the stent is held in the desired position such that the stent expands.

There are both self-expanding and non-self-expanding stents. The self-expanding type of device is made with a material having an elastic restoring force, whereas a non-self-expanding stent is often made with elastic, plastically deformable material. It is positioned over a mechanical expander, such as a balloon, which can be inflated to force the prosthesis radially outward once the desired site is reached.

SUMMARY OF THE INVENTION

In a preferred embodiment, the invention features an implantable medical stent having a low profile during delivery. The stent is a tubular body with a body wall structure having a geometric pattern of cells defined by a series of elongated strands extending to regions of intersection. An example of a stent having a cell shape in accordance with the invention can be found in U.S. Ser. No. 08/743,395, filed Nov. 4, 1996, the entire contents of which is incorporated herein by reference. This stent cell structure utilized helically wrapped joints to connect the different strands to form a tubular body.

A limitation on the use of the helically joined stent involved the minimum constrained diameter of the stent during delivery. Because of the helically wrapped joints abutting one another along a given circumference, the minimum constrained diameter of the stent was 9 French (3 mm). For example, the length of the helically wrapped joint for a strand having a diameter of 0.006 inches in the constrained position is 0.045 inches. For a five cell structure having five helically twisted abutting joints, this results in a constrained circumference of 0.228 inches with a diameter of 0.072 inches. However, there are many applications in which it is necessary to achieve a smaller constrained diameter to provide delivery, for example, through smaller lumens within the vascular system, to reduce trauma during percutaneous delivery, or to provide endoscopic delivery through small diameter channels of endoscopes.

To achieve a smaller constrained diameter of 8 French or less, for example, a preferred embodiment of the invention replaces one or more of the helically wrapped joints along any given circumference with a simple crossed joint in which one strand crosses either above or below a second strand. Thus, the strands at a crossed joint can move more freely relative to each other, but this structure reduces the minimum circumference as the length of one or more helically twisted joints has been removed. This can reduce the constrained diameter by 50%.

In another preferred embodiment of the invention, the stent can include a first tubular body made from a first group of strands and a second tubular body surrounding the first tubular body and made from a second group of strands. This type of structure can be used to fabricate a low-profile device having sufficient radial expansion force for a self-expanding stent without a substantial change in foreshortening. This embodiment can include, for example, three or four helically wrapped joints along any circumference of the first and second tubular bodies in which the joints of the two bodies are offset in the constrained state. This embodiment also significantly improves the ratio of the displayed diameter to the constrained diameter.

The strands of the first group can have a different shape, diameter or material from the strands of the second group such that the inner body has a larger radial restoring force than the outer body and can thereby impart the outward force to the outer body.

In one embodiment, the strands of the inner body can be thicker than the strands of the outer body and can be interleaved with the outer body along the entire length of the stent. In another preferred embodiment, the inner and outer bodies can be interlocked at one or both ends. This can permit the use of a cover between the inner and outer bodies along a certain portion of the stent. The use of the cover can enhance epithialization between the wall of the lumen and the outer body, reduce migration of the stent in certain applications and can prevent tumor in-growth. The cover can also provide a supporting matrix for drug delivery.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 4A and 4B illustrate a mandrel for making a stent of FIGS. 2A, 2B, and 3;

DETAILED DESCRIPTION OF THE INVENTION

Figure 1A:
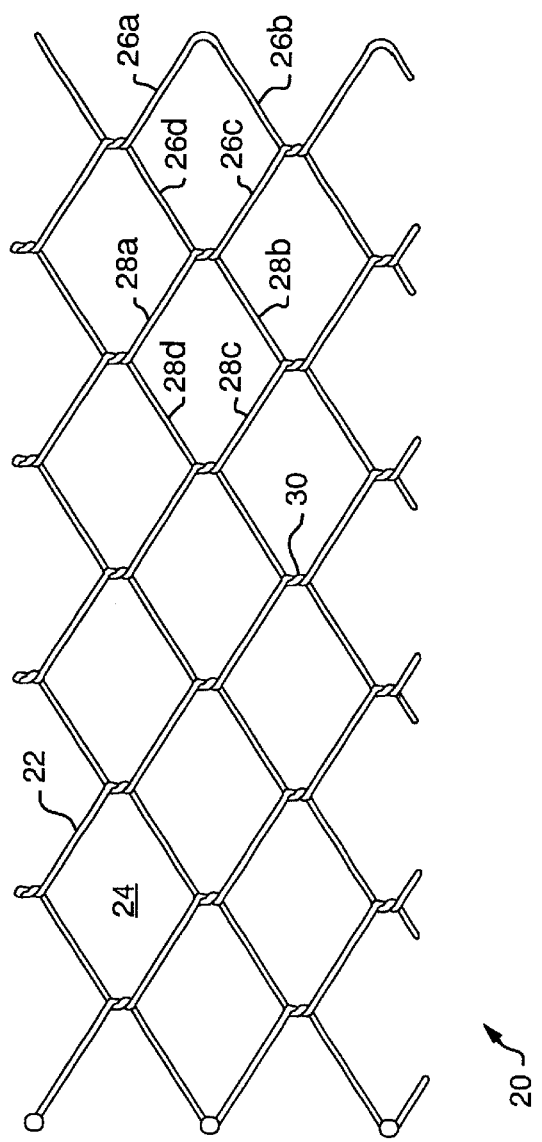
FIG. 1A is a flat layout view along the longitudinal axis of a stent.

Referring to the drawings in detail, where like numerals indicate like elements, there is illustrated a stent in accordance with the present invention designated generally as 10.

Medical prostheses, such as a stent 10 according to the invention, are placed within the body to treat a body lumen that has been occluded. Stents according to the invention are formed of wire configured into a tube and are usually delivered into the body lumen using a catheter. The catheter carries the stent in a reduced-size form to the desired site. When the desired location is reached, the stent is released from the catheter and expanded so that it engages the lumen wall as explained below.

A stent 20 is shown in a flat layout view in FIG. 1A. The stent 20 is formed of elongated strands 22 such as elastic metal wires. The wires 22 are woven to form a pattern of geometric cells 24. The sides 26a, 26b, 26c, and 26d of each of the cells 24 are defined by a series of strand lengths 28a, 28b, 28c, and 28d. Each of the sides 26 are joined to the adjoining side at an intersection where the strands 22 are helically wrapped about each other to form interlocking joints 30.

Figure 1B:
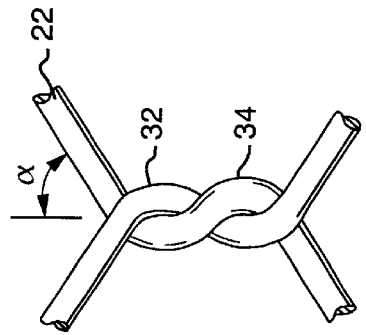
FIG. 1B is an enlarged portion of the stent taken at section 1B—1B in FIG. 1A.

Referring to FIGS. 1A and 1B, the interlocking joints 30 are loose and spaced from each other in the full expansion position. The cells 24 have a diamond shape. The strand angle is α. When the stent 20 is radially compressed, the interlocking joints 30 are in tight interference such that points 32 and 34 are in close proximity. In addition, the interlocking joints 30 on the same circumference are in close contact, therefore establishing the compressed, reduced size which can be fit within a sleeve for delivery on a catheter. The strand angle α is increased in the compressed or constrained state of the stent. A medical prosthetic stent and method of manufacturing such a stent is described in U.S. patent application Ser. No. 08/743,395 which was previously incorporated herewith by reference.

Figure 2A:
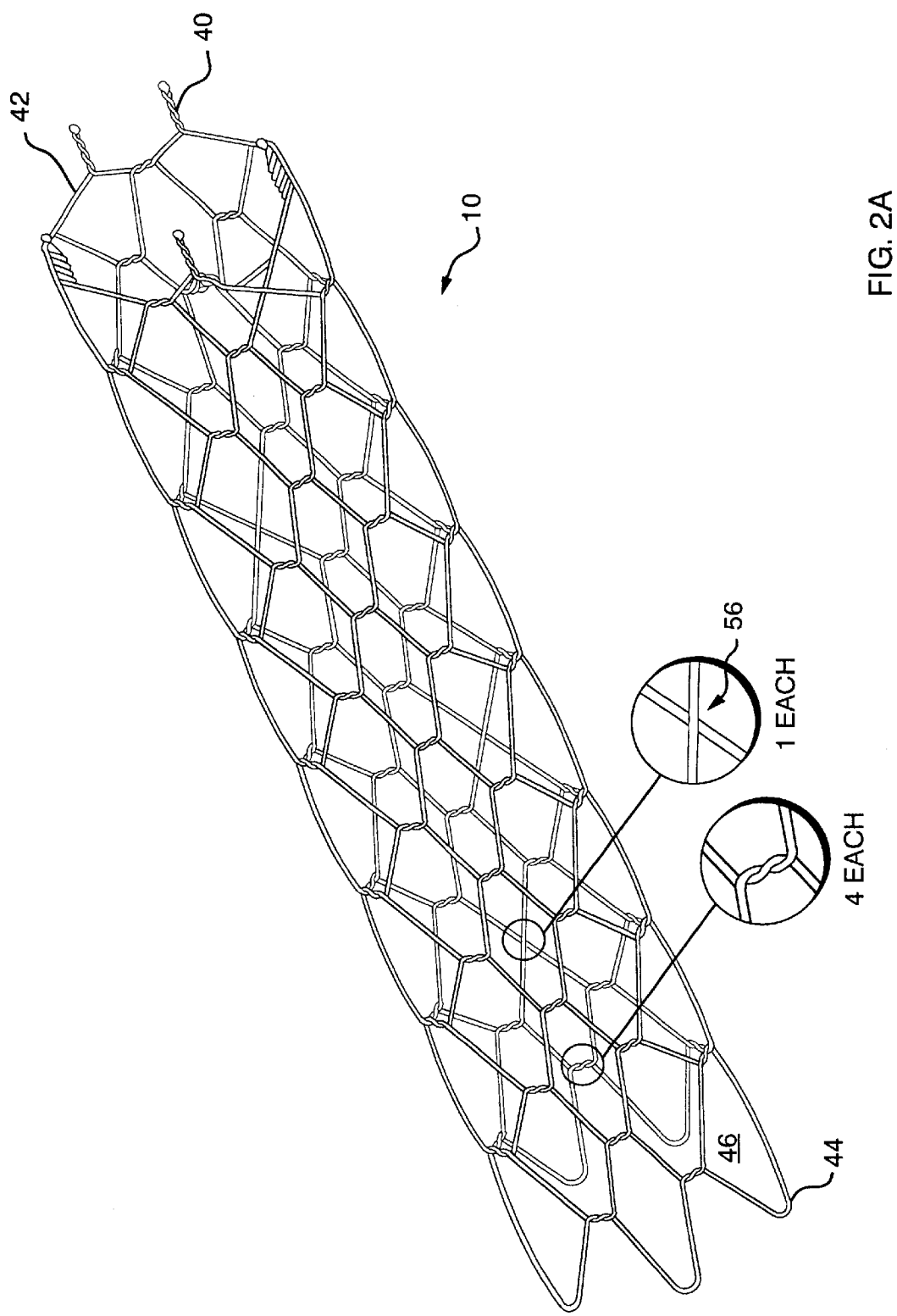
FIG. 2A is a perspective view of a stent according to the invention.

Referring to FIG. 2A, an isometric view of stent 10 according to the invention is shown in an expanded position. The stent 10 is formed from a plurality of strands 42. In a preferred embodiment, there are five strands 42, as seen in the layout view of FIG. 2B. The strands 42 are woven in a pattern starting at a proximal end 44. The pattern forms a plurality of geometric cells 46. Each strand 42 forms a pair of sides 48a and 48b of the most distal cell 46. Each of the sides, with the exception of at least one as explained below, are joined to the adjoining side at an intersection 52 where the strands 42 are helically wrapped about each other to form interlocking joints 54.

Figure 2B:
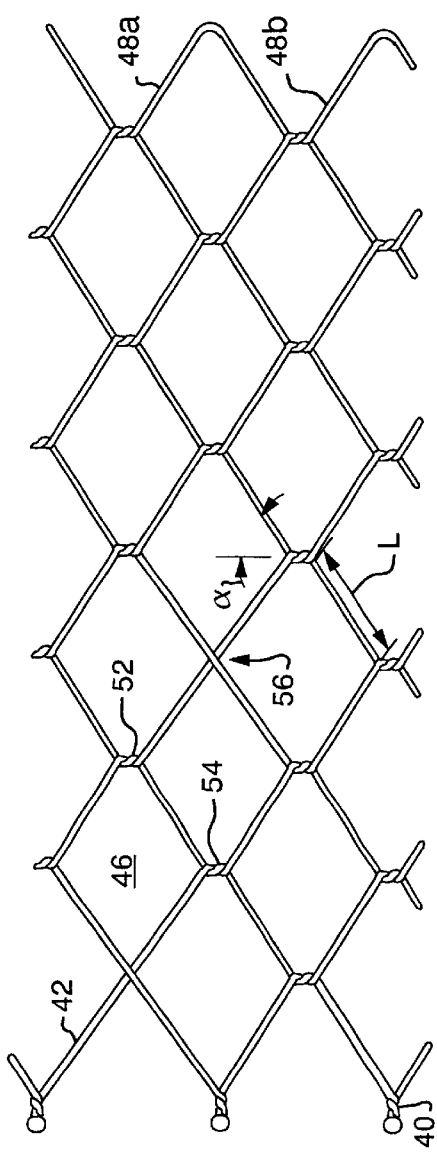
FIG. 2B is a flat layout view of an expanded low profile stent of FIG. 2A.

While there are five intersections 52, at least one of the intersections 52 is formed by strands 42 that just cross forming a cross joint and are not twisted to form a wrap as indicated at point 56 in FIG. 2B. A preferred pattern of where the strands 42 just cross is spaced 1½ cells 46 away, as seen in FIG. 2B.

Figure 3:
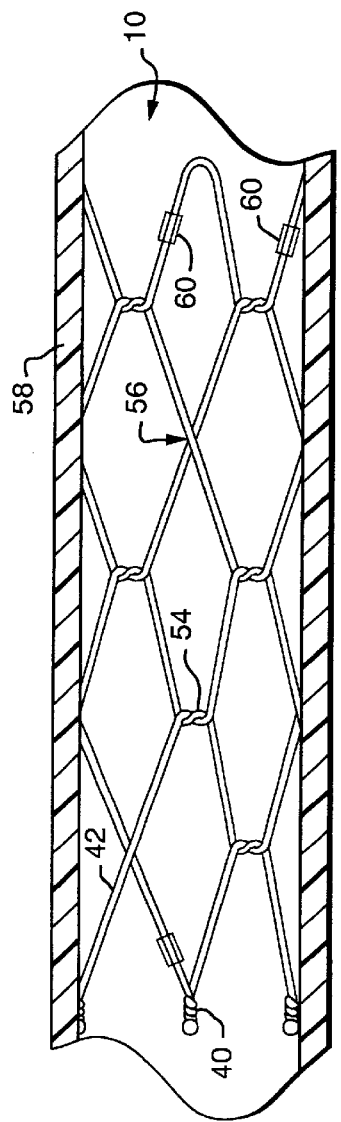
FIG. 3 is an enlarged cross-sectional view of a delivery tube containing a low profile diamond metal stent.

Referring to FIG. 3, the stent 10 is shown in the contracted position within the sleeve 58. Similar to the embodiment shown in FIGS. 1A and 1B, the size to which the stent 10 can be constricted is limited by where the interlocking joints 54 engage each other. The elimination of one wrap joint allows for the stent 10 to be compressed to a smaller size.

In a preferred embodiment, the strands 42 are formed of nitinol wire. The wires each have a diameter of 0.006 inches. The stent 10 has an outside diameter when fully expanded of 10 millimeters. The stent 10 is capable of compressing into a sleeve 58 of an outside diameter of 8.0 French or less, and preferably 7.0 French (3fr=1 mm). The stent shown in the FIGS. 1A and 1B, of similar material and dimension, is capable of compressing to a diameter of approximately 9 fr.

In one preferred embodiment, the length of the legs or sides 48 of the cells 46 is similar to that of the embodiment shown in FIGS. 1A and 1B. The radial force is decreased from the elimination of one of the interlocking or wrap joints. The compressed stent 10 has a length of approximately 120 of the expanded stent. Therefore, for a 10 centimeter stent, the compressed length is 12 centimeters.

In one preferred embodiment, the length of the legs or sides 48 of the cells 46 are reduced. The reduced length is to compensate for a decrease in radial force resulting from the elimination of one of the interlocking or wrap joints. The compressed stent 10 has a length of approximately 150 of the expanded stent. Therefore, for a 10 centimeter stent, the compressed length is 15 centimeters.

In one preferred embodiment, a plurality of (ten shown) platinum-iridium radiopaque (R.O.) markers 60 are located on the stent 10. The R.O. markers 60 are threaded onto the terminating cells; five on the proximal end and five on the distal end.

A method of making the stent is shown in FIGS. 4A and 4B. A mandrel 62 has a plurality of pins 64 on the outer surface of the mandrel in a pattern that determines the geometric cell 46 pattern. The strands 42 are bent around the top portion 66 of each top anchoring pin 64 to form the proximal end 44 of the stent 10. The strands 42 are then pulled diagonally downward to an adjacent anchoring pin 64 where the strands 42 are joined. The strands 42 are helically wrapped about each other to form the interlocking joint 54, with each strand passing through a single 360 degree rotation. The two strands are pulled taught so that the interlocking joint 54 rests firmly against the bottom portion 68 of the anchoring pin 64 such that each strand 42 is maintained in tension.

Each level of anchoring pins 64 is missing a pin 64 in a set order, such as to achieve the desired pattern in FIG. 2B. The stands 42 which pass the missing pin location simply cross to form the cross joint.

In a preferred embodiment, the anchoring pins 64 are square. The square pins retain the helically wrap of the strands in a proper position. In a preferred embodiment, the pins have a width of 1 millimeter. The anchoring pins can have a smaller width such as 0.5 mm for use with narrower diameter strands, such as 0.005 inch diameter strands.

The free ends of the strands 42 are then pulled downward to the next diagonally adjacent anchoring pin 64. This process is continued until the desired length of the stent 10 is achieved.

The stent 10 is then heat-treated. The strands 42 at the joining end 40 of the stent 10 are attached, for example, by ball welding the ends of the wires. The heat-treating and alternative finishing techniques are described in U.S. patent application Ser. No. 08/236,786 which was filed on Apr. 29, 1994, the entire contents is incorporated herein by reference.

Another alternative to the R.O. markers 60 for locating the stent 10 using fluroscopy is to coat the stent with gold.

The stent 10 can be either totally or partially coated. In a partially coated stent, only portions of the strands between the joints are coated. Coating of a stent is described in further detail in U.S. Pat. No. 5,201,901 which issued on Apr. 13, 1993, the entire contents is incorporated herein by reference.

Figure 5B:
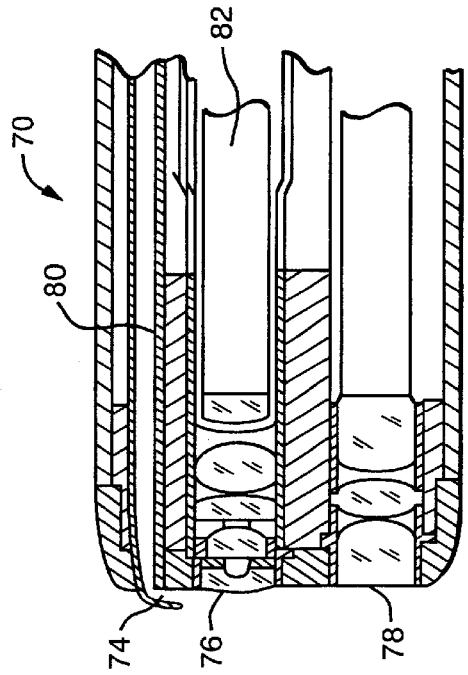
FIG. 5B is a sectional view of the distal end of the endoscope.
Figure 5A:
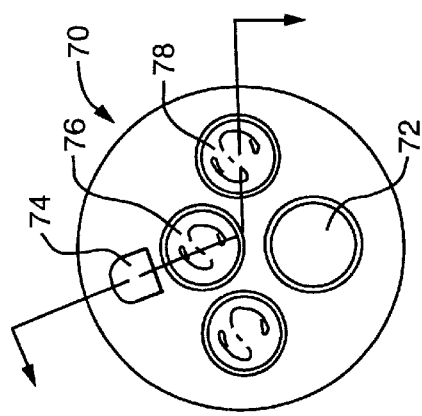
FIG. 5A is a distal end view of an endoscope.

In one preferred embodiment, the stent 10 is installed using an endoscope 70 as seen in FIGS. 5A and 5B. The endoscope 70 has a channel 72 which is typically used for collecting biopsy samples or for suction. This channel 72 is how the stent 10 is passed into the body as explained below. The endoscope 70 in addition has an air/water nozzle 74 for cleaning the area in front of the endoscope 70. In addition, the endoscope 70 has a mechanism for the physician to see what is in front of the endoscope 70; this mechanism includes an objective lens 76. A pair of illumination lenses 78 which are used in lighting the site are also shown.

FIG. 5B illustrates a cross sectional view of the distal end of the endoscope 70. An air/water tube 80 extends down to the air/water nozzle 74. Both the viewing mechanism and the illumination mechanism have optical fiber bundles 82 leading to the respective lens 76 and 78.

Endoscopes come in various sizes and lengths depending on the purpose. The channel 72 likewise has different sizes. It is recognized that it may be desirable to use a smaller diameter scope to be less invasive or that a larger diameter scope will not fit the lumen. The following table is an example of various size endoscopes.

| Working Length (cm) | Distal Tip O.D. (mm) | Channel Diameter (mm) |
| --- | --- | --- |
| 55 | 4.8 | 2.0 |
| 55 | 6.0 | 2.6 |
| 63 | 12.2 | 3.2 |
| 102 | 9.8 | 2.8 |
| 102 | 12.6 | 3.7 |
| 124 | 11.0 | 2.8 |
| 124 | 11.0 | 3.2 |
| 125 | 11.3 | 4.2 |
| 173 | 13.0 | 3.2 |

The stent 10 as described in relation to FIGS. 2A–4B can be used with channels of 3.2 mm or greater as described below.

Figure 6B:
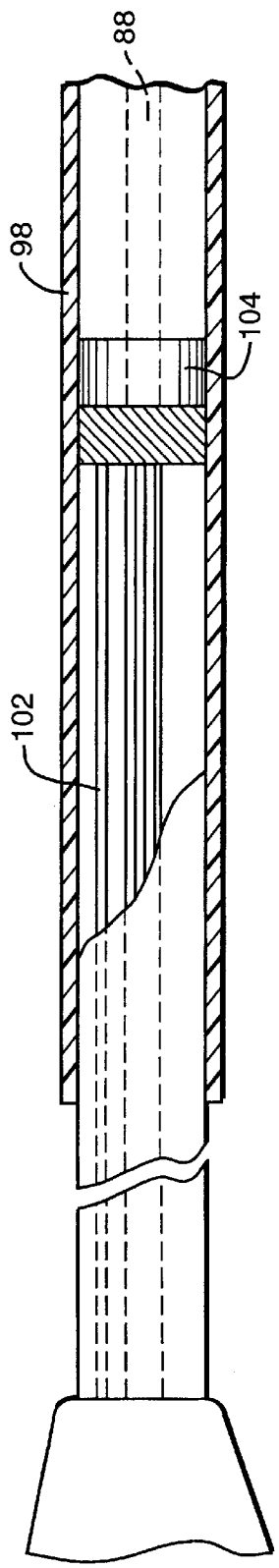
FIG. 6B is an enlarged view of the middle section of the "over-the-wire" delivery system.
Figure 6A:
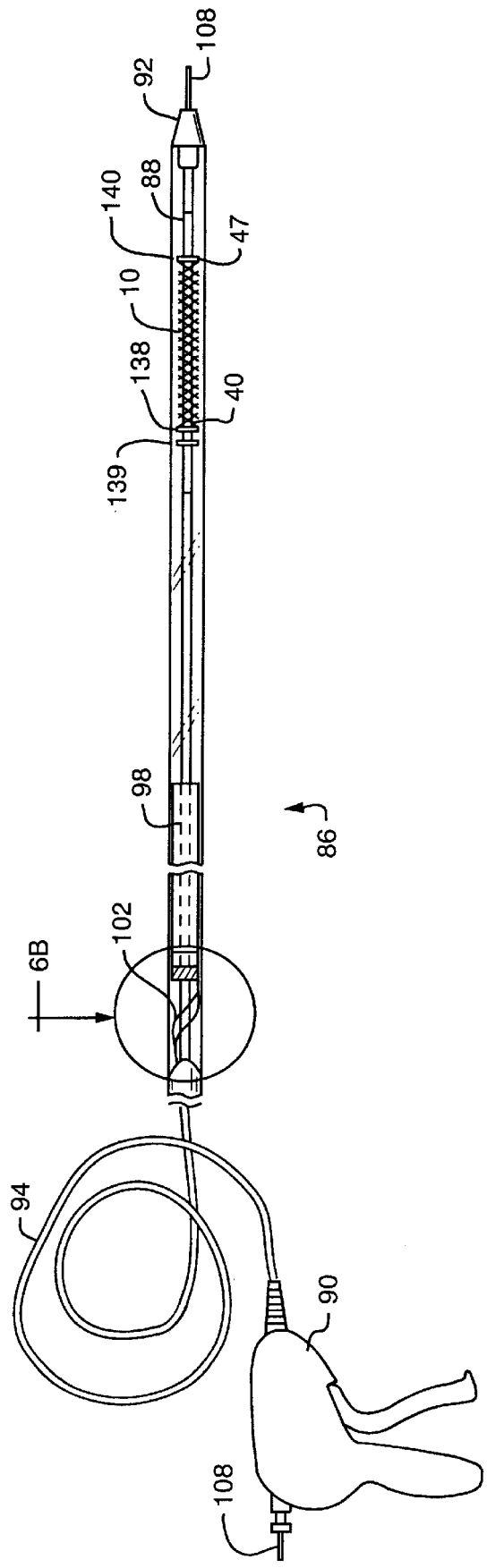
FIG. 6A is an "over-the-wire" delivery system.

In addition, the stent 10 can be introduced using a percutaneous insertion. In both the method using the endoscope 70 and the percutaneous procedure, an over the wire delivery system 86 as seen in FIG. 6A can be used. The over-the-wire delivery system 86 has an elongated catheter 88 over which the stent 10 is positioned. The catheter 88 extends from a proximal handle 90 to a distal tip end 92. The catheter 88 extends through a shaft 94 at the proximal end.

An outer sheath 98 is located at the distal end of the over the wire delivery system 86. The outer sheath 98 is moved towards the handle 90 using a pull wire 102 and a pull ring 104 as seen in FIG. 6B. A guidewire 108 extends through the catheter to the distal end tip 92, as best seen in FIG. 6A.

In a preferred embodiment, the outer sheath 98 has an outer diameter in the range of between 0.072 inches and 0.094 inches. The inner diameter of the outer sheath 98 has a range of between 0.066 inches and 0.086 inches. The outer sheath tends to the lower portion of the range when the stent can contract to the 6 French size and towards the upper portion of the range when the stent can contract to the 7 French size.

In one preferred embodiment, the outer sheath 98 is formed having several layers of material. The nominal outer diameter is 0.093 inches and a nominal inner diameter of between 0.078 and 0.081 inches. The inner layer is composed of polyethylene or TFE and has a nominal thickness of 0.001 inches. A layer of EVA or polyurethane of a nominal thickness of 0.0005 inches forms the second layer. A braid metal spring stainless or liquid crystal polymer fiber having a thickness of 0.0015 to 0.0025 inches overlies the second layer and forms the core of the outer sheath 98.

In a preferred embodiment, the fourth layer varies in material composition as it extends from the proximal end to the distal end. The proximal end of the sheath is formed of Pebax or polyamide and the material varies to a polyamide or cristamid at the distal end. This layer has a nominal thickness of 0.002 inches. This varying of the material is for increased flexibility at the distal end to move through tortures easier and increased rigidity at the proximal end to give the catheter better push.

The sheath 98 has a finish layer of a hydrophlic coating having a thickness of between 0.0005 and 0.001 inches. The coating is for increase lubricativity.

The shaft has an outer diameter of 0.074 inches (1.88 mm). The shaft is formed of nylon 12 cristamid or cristamid.

In a preferred embodiment, the tip extrusion has an outer diameter in the range of between 0.042 and 0.055 inches. The inner diameter of the tip extrusion has a range of between 0.036 and 0.040 inches.

In one preferred embodiment, the tip extrusion or catheter has a nominal outer diameter of 0.047 inches and an inner diameter of 0.037 inches. The inner diameter defines the passage for the guidewire. In a preferred embodiment, the catheter is formed of Peek (Polyether ether ether Keetone) Peek Braid Peek, Polyimide or Polyimide Braid Polyimide. In a preferred embodiment, the guide wire 108 has a diameter of 0.035 inches.

Figure 7:
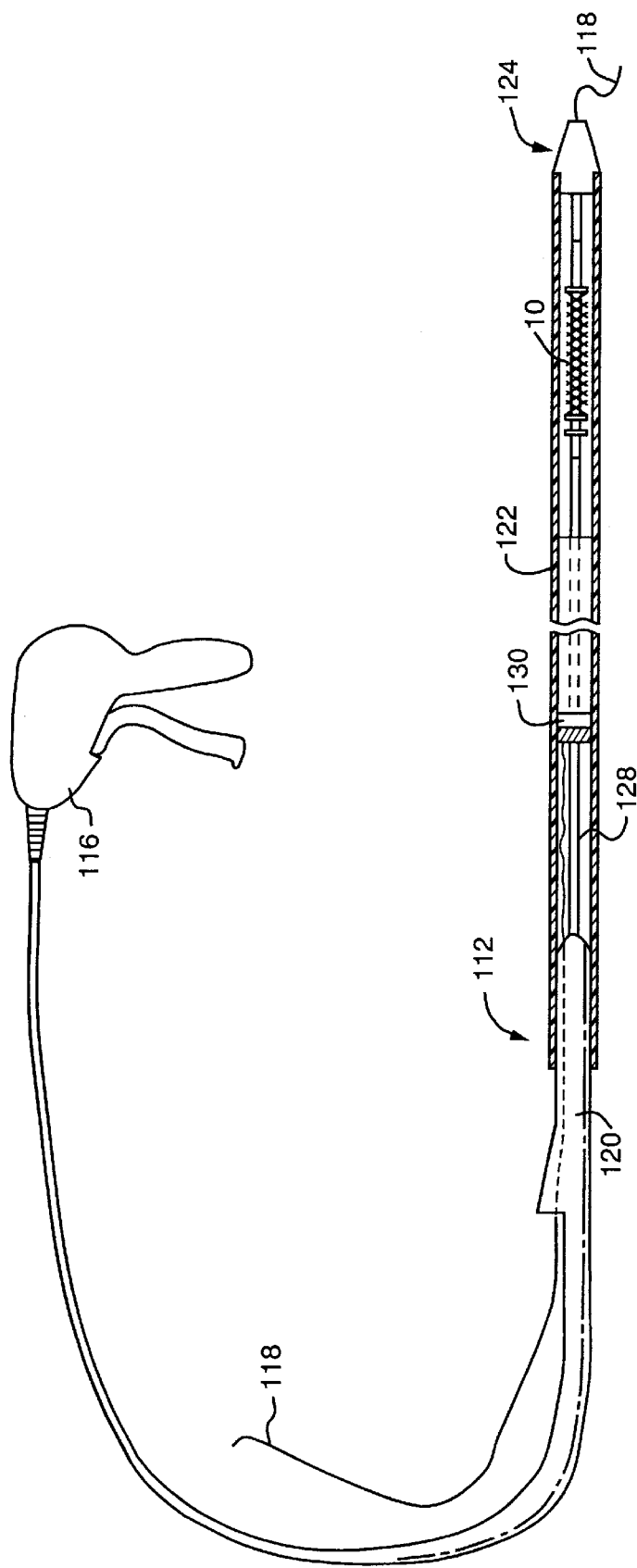
FIG. 7 is a rapid exchange delivery system.

An alternative method to the over-the-wire delivery system 86 shown in FIGS. 6A and 6B is a rapid exchange delivery system 112 shown in FIG. 7. The rapid exchange delivery system 112 has a shaft 114 that extends from a proximal handle 116. A guidewire 118 extends from a two lumen transition zone 120 through an outer sheath 122 to a distal tip end 124. In contrast to the over the wire delivery system 86, the guide wire 118 does not extend all the way back to the proximal handle 116. Similar to the over the wire delivery system 86, the outer sheath 122 of the rapid exchange delivery system 112 is moved towards the handle 116 using a pull wire 128 and a pull ring 130.

Referring to FIGS. 8A–8F, the over-the-wire delivery system 86 of FIGS. 6A and 6B is shown for positioning a stent 10 in a bile duct. Stents are used in many uses including for treatment of an obstruction 134, such as a tumor in the bile duct. The delivery system can position a prosthesis, such as a stent 10, to move the obstruction out of the lumen 136.

Typically, the occlusion substantially closes off a lumen, such as a bile duct which has a healthy diameter of about 8–10 mm. The obstruction may be several centimeters in length. After the obstruction is located using one of several diagnostic techniques, the physician gains access to the lumen. Using ultrasound or fluoroscopy, the guidewire 108 such as seen in FIG. 8C, is positioned through the outer access sheath 98 so that it extends past the obstruction.

Referring to FIG. 6A, the delivery system 86 is advanced axially and distally until the distal radiopaque marker 60 is positioned axially at a location at least about 1 cm distal of the occlusion 134. This location substantially corresponds to the position at which the distal end 47 of the stent 10, when expanded, will engage the lumen wall 136. The location is selected so the stent 10 is positioned beyond the occlusion 134 but not too close to the end of the bile duct, for example. The marker 138 indicates the position of the proximal end 40 of the stent 10 in the expanded position and is such that the proximal end 40 of the prosthesis will engage healthy tissue over a length of at least 1 cm. Where possible the stent 10 is centered about the obstruction, based on the fully expanded length indicated by markers 138 and 140. The marker 139 indicates the proximal end of the stent when the stent is in the fully compact form, which has an overall length of approximately 20 percent longer than in its expanded state. Therefore for a stent of 7.5 centimeters, the compressed state has a length of approximately 9 centimeters.

Figure 8A:
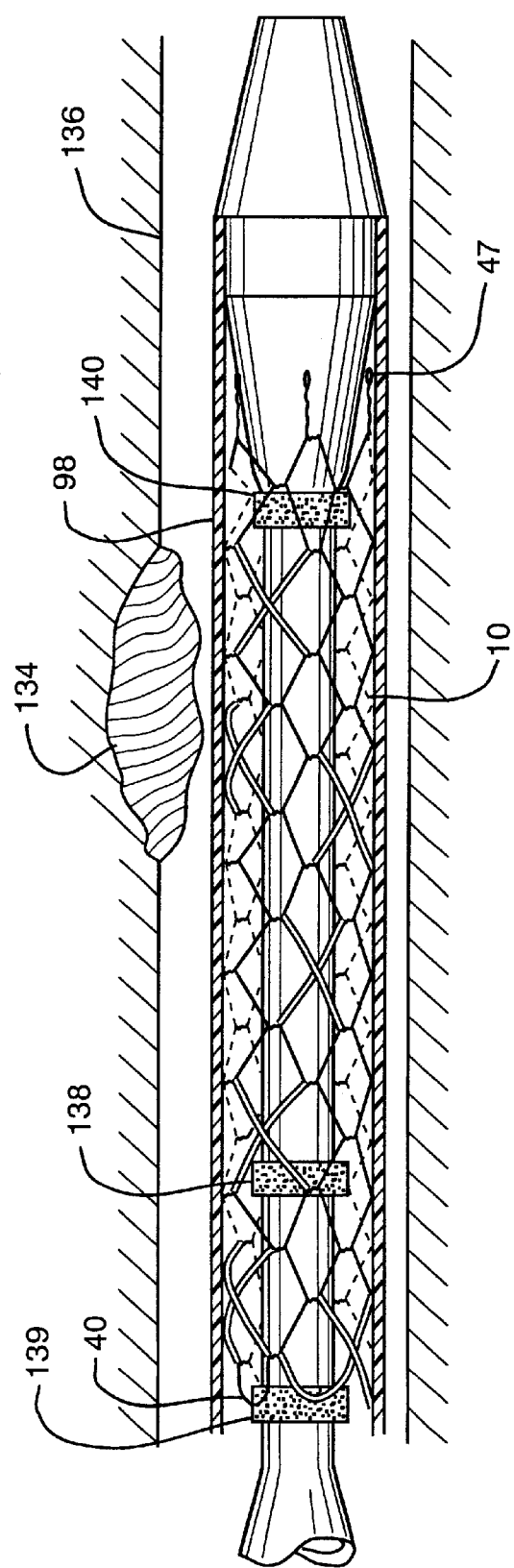
FIGS. 8A–8E illustrate the operation of the delivery of the stent.
Figure 8B:
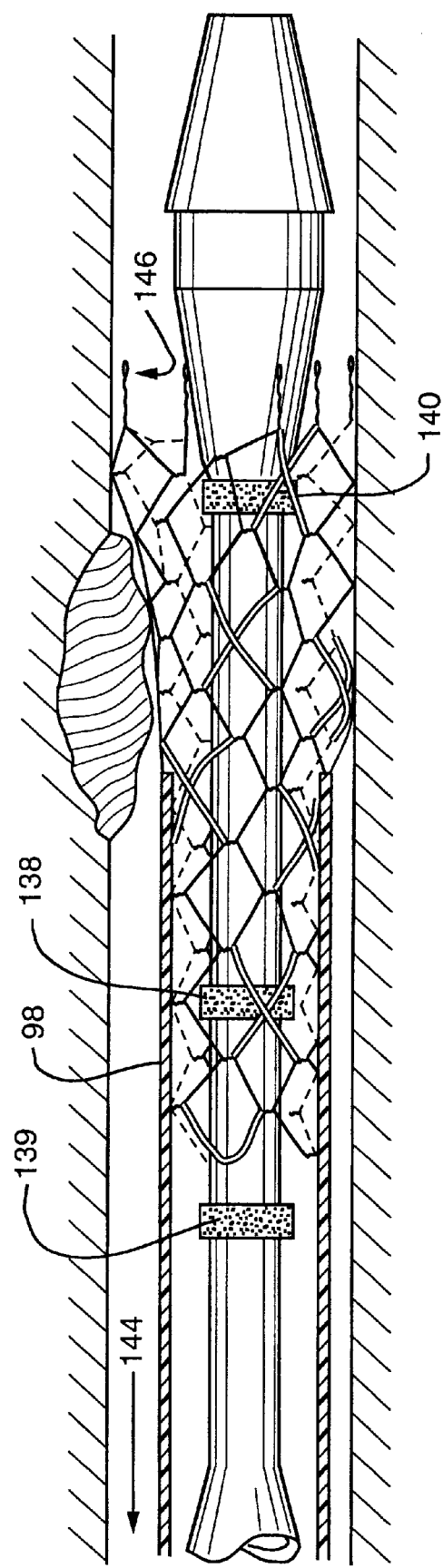

The sheath 98 is retracted in one continuous motion as illustrated in FIG. 8B. With the sheath 98 partially withdrawn, (arrow 144), portions of the stent 10 expand (arrow 146). The lengthening of the stent 10 has a simultaneous effect of reducing the radial force the stent exerts on the wall of the sheath 98 and, therefore, reducing the frictional force between the inner wall of the sheath and the stent 10, allowing a smoother retraction of the sheath 98 with less axial force.

Figure 8C:
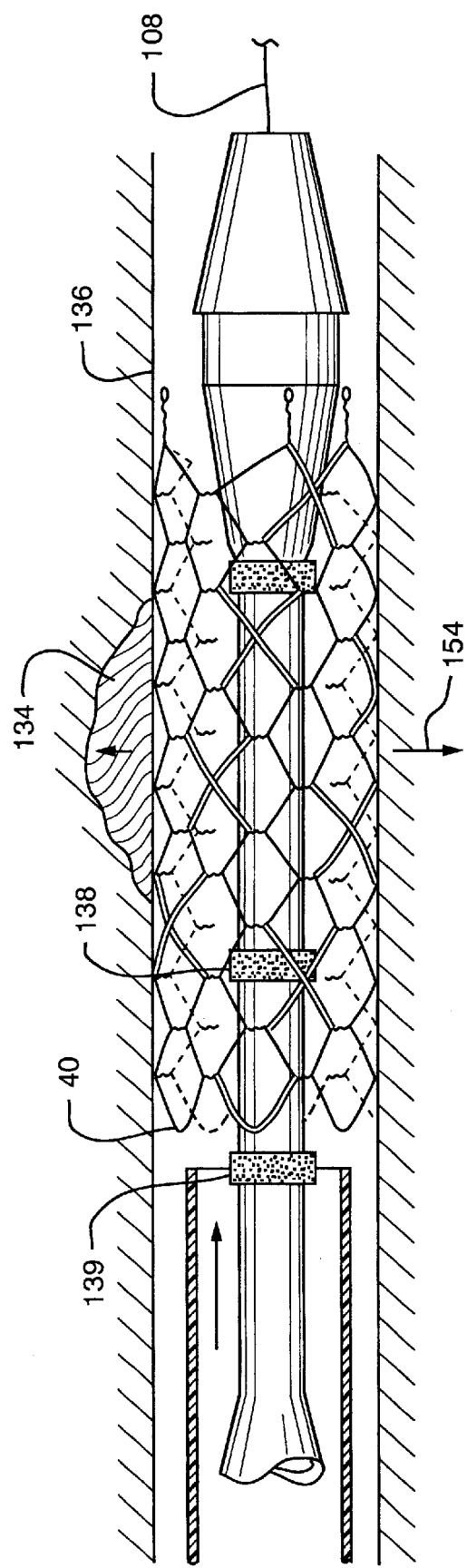

After sheath retraction continues but usually to a point less than the marker 138, the proximal end 40 of the expanding and contracting prosthesis 10 exits the sheath 98 and engages the lumen wall 136, forcing open the lumen 136 to its normal diameter and firmly anchoring the stent so that it resists axial motion, as illustrated in FIG. 8C.

Figure 8D:
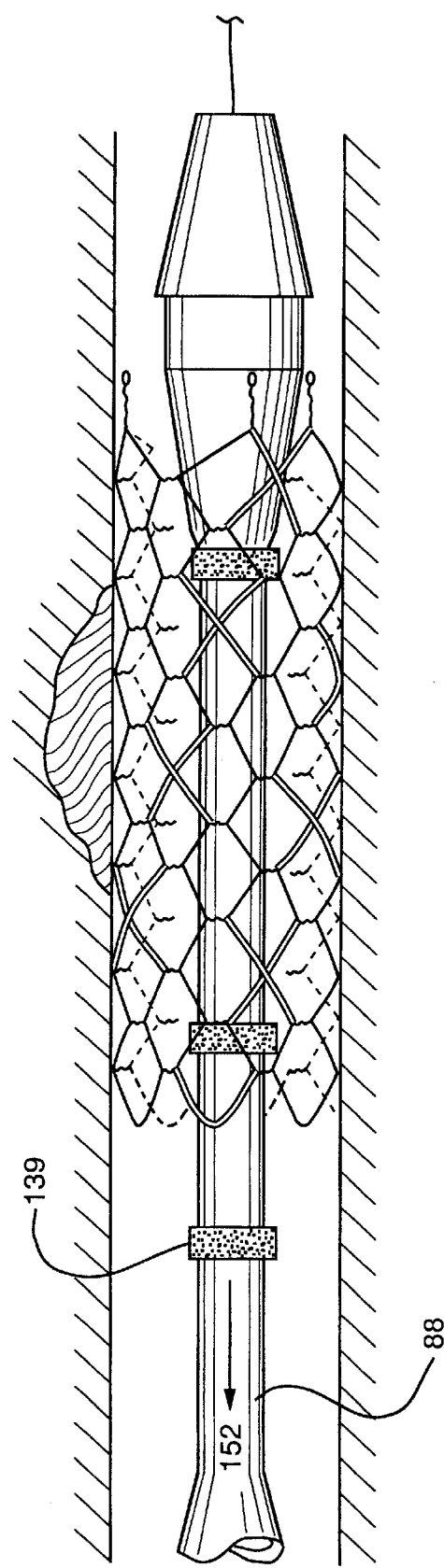

The stent is released entirely from the catheter body 88 by drawing the catheter body 88 proximally (arrow 152) as seen in FIG. 8D, which causes the end loops to be positioned at more distal positions along the members, until the radial force of the stent 10 causes the members to deflect outwardly (arrows 154).

Figure 8E:
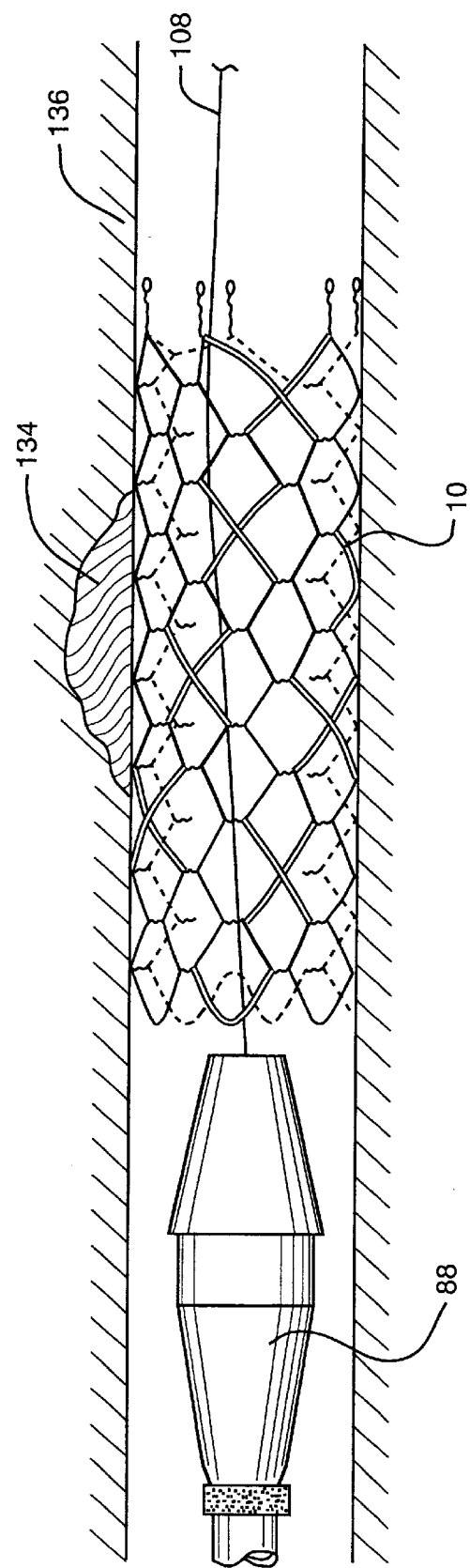

The catheter 88 is then removed from the body, leaving the prosthesis 10 properly positioned as illustrated in FIG. 8E.

Figure 9:
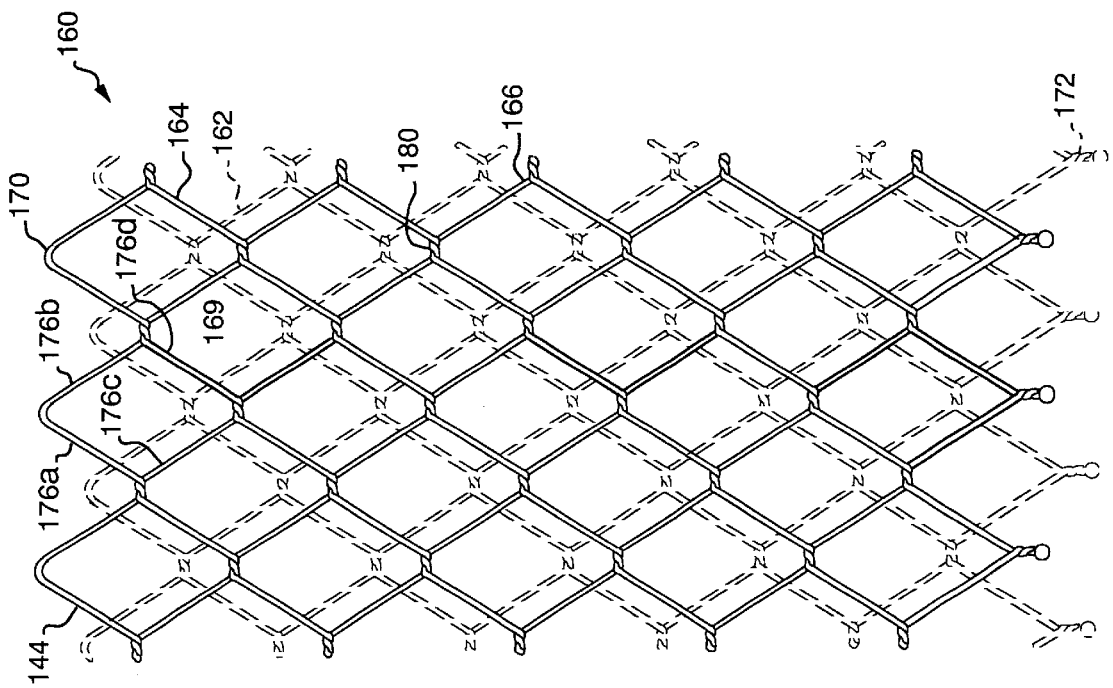
FIG. 9 is a flat layout view of a double layer stent.

An alternative embodiment of the low profile diamond stent is shown as a flat layout view in FIG. 9. The stent 160 has two separate layers 162 and 164; an inner layer 162 shown in hidden line and an outer layer 164. Each layer 162 and 164 of the stent 160 has a plurality of strands 166. In a preferred embodiment, each layer has four strands; this is in contrast to the five strands in the previous embodiment.

The strands are woven in a pattern of geometric cells 169 starting at the distal end 170. Each strand 166 forms a pair of legs 144 of the most distal opening on the cell 168. The inner layer 162 and the outer layer 164 are intertwined at both the distal end 170 and the proximal end 172.

The sides 176a, 176b, 176c, and 176d of each of the cells 168 are defined by a series of strand lengths 178a, 178b, 178c, and 178d. Each of the sides 176 are joined to this adjoining side at an intersection where the strands are helically wrapped about each other to form interlocking joints 180.

Similar to the embodiment shown in FIGS. 1A and 1B and in contrast to the previous embodiment, every intersection has an interlocking joint 180. Without the fifth strand 166, the stent 160 can be contracted into a smaller diameter than that of the stent 20 shown in FIGS. 1A and 1B.

In a preferred embodiment for use in a colon, both layers are formed of identical materials. Each strand is composed of nitinol and has a diameter of 0.010 inches.

The two separate layers 162 and 164 in the constricted position are off-set from each other so the interlocking joints of one layer do not engage with the interlocking joints of the other layer. The off-set between layers is created by an off-set created when formed as described below or created by the related motion of the layers as the layers are constricted. The related motion can be the result of the constraints of the strands or the material properties. One property difference can be the thickness of the strands as described in the next embodiment.

The stent can be coated with a silicon lubricant or suitable lubricant to ease the self-expanding of the stent.

Figure 10:
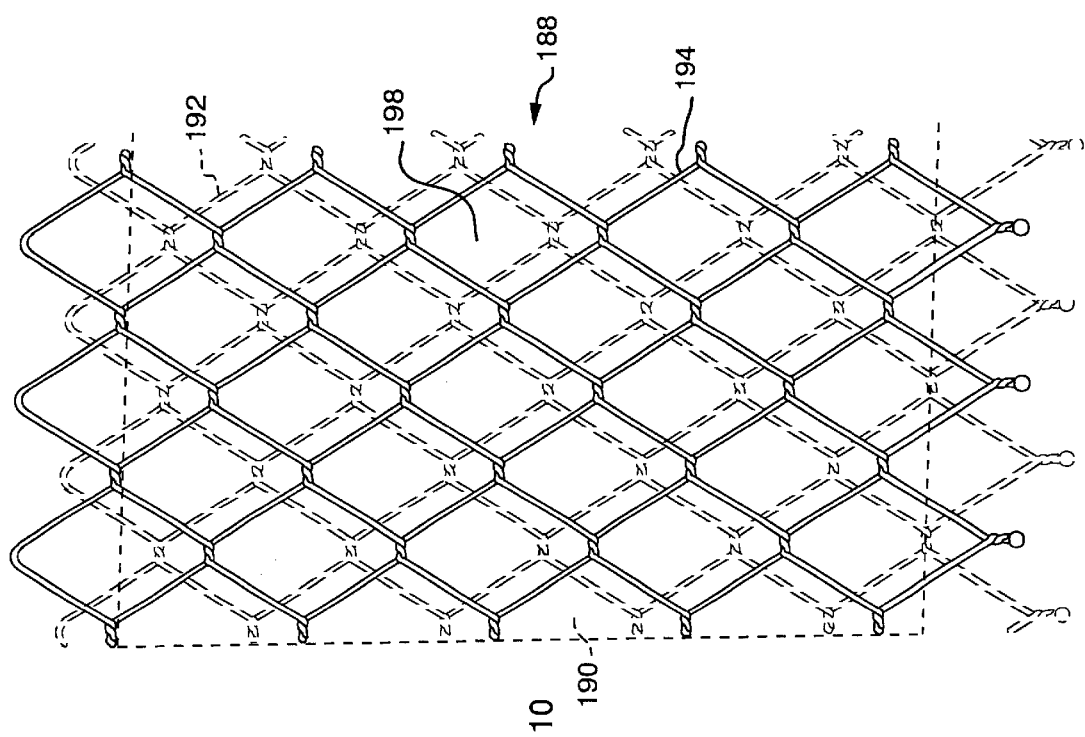
FIG. 10 is a flat layout view of an alternative embodiment of a double layer stent.
Figure 12:
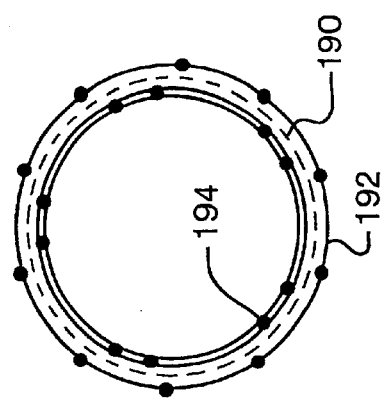
FIG. 12 is a cross sectional view of the double layer stent with the interposed cover taken along line 12—12 of FIG. 11.
Figure 11:
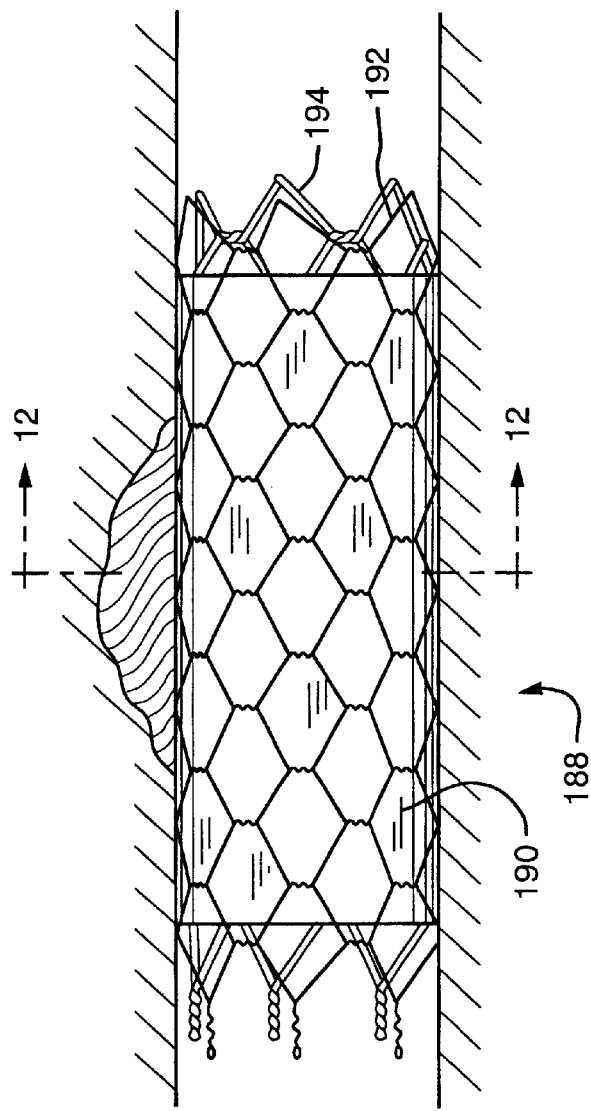
FIG. 11 is an enlarged cross sectional view of the double layer stent of FIG. 10 with an interposed cover in an artery.

An alternative embodiment of the double layer stent 160 of FIG. 9 is shown in FIGS. 10–12. In contrast to the double layer stent 160 of FIG. 9, the double layer stent 188 has a cover layer 190 interposed between an outer layer 192 and an inner layer 194. The outer layer 192 is shown in hidden line and the cover layer 190 is shown in hidden line in FIG. 10.

Similar to the previous embodiment, the inner layer 194 and the outer layer 192 are intertwined at both the proximal end 170 and the distal end 172. The intertwining of the layers 192 and 194 retains the cover layer 190 in position.

In a preferred embodiment, each layer has four strands and are woven similar to the embodiment shown in FIG. 8 to define the geometric cells 198. The strands of the two layers are formed of two different thickness wires in a preferred embodiment. The inner layer has a thicker wire.

FIG. 11 shows the stent in an artery. The stent is moving an obstacle out of the passage. The cover prevents tumor in-growth, will seal fistulas and block aneurysms.

One technique for placing a stent into the circulation system of a patient is to enter from the brachial artery located in the arm. This point of entry can be used for insertion into the vascular system including for example, peripheral locations such as the knee which require the flexibility of the diamond stent.

A cross-sectional view of the stent 188 is shown in FIG. 12. The inner layer 194 having the thicker strands forces the cover 190 and the outer layer 192 outward. The over 190 is in engagement with both the inner layer 194 nd the outer layer 192.

In a preferred embodiment, the strands are formed of nitinol. The inner layer has strands having a diameter of 0.006 inches. The strands of the outer layer have a diameter of 0.005 inches. The radial expansion force of the thicker wire inner layer is transmitted to the outer layer. The radial expansion force can be altered by varying one or both layers.

In another preferred embodiment, the stent has three strands on each layer. The inner layer has a diameter of 0.008 inches. The strands of the outer layer have a diameter of 0.005 inches.

The outer layer can be formed from a non self-expanding material. The outer layer can be chosen for its radiopaque characteristics. Materials that can be chosen for their radiopacity characteristics include tantalum, platinum, gold or other heavy atomic metal.

In a preferred embodiment, a cover is interposed between the layers. The cover can be made of several types of material which allow the stent to be compressed to a small diameter and also be self-expanding. A preferred material is a woven carbon fiber, a metal mesh, a polymer such as a polyurethane, or a material treated with a drug for time release. Different agents can be employed on the inside and the outside. An electrical current can be applied to tissue using the stent. Different materials for the layers can be used than the interposed cover depending on the treatment site and the desired method of treatment.

Figure 13:
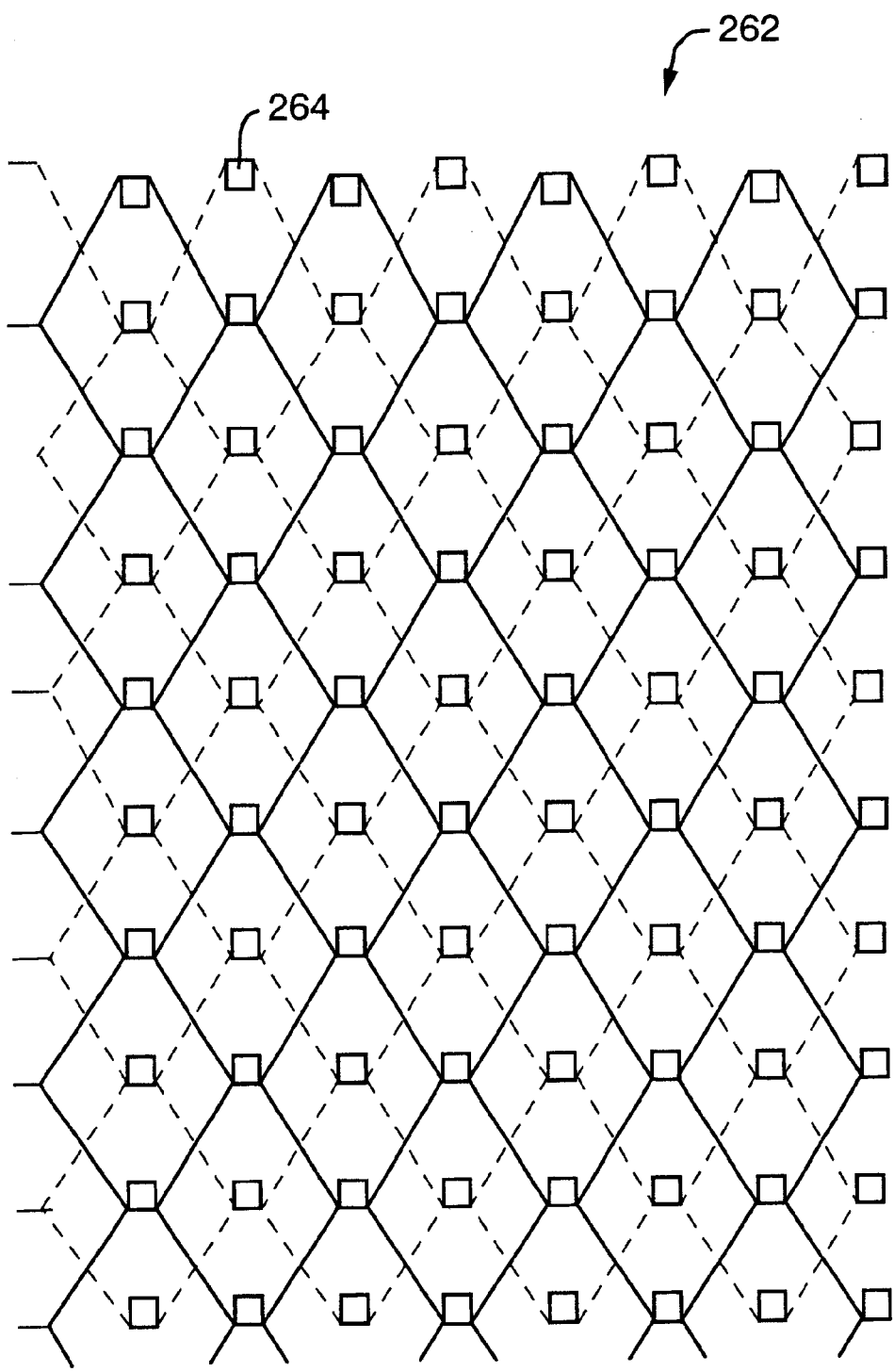
FIG. 13 illustrates a mandrel for making a stent of FIGS. 9 or 10 and 11.

In one preferred embodiment, the layers 192 and 194 are interwoven for the entire stent without an interposed cover. Referring to FIG. 13, a mandrel 262 has a plurality of anchoring pins 164. For a stent having two layers of four strands each, each row has eight (8) anchoring pins 164 at the same height. The top row, however, has the anchoring pins 164 for one strand positioned ½ millimeter higher than the other set. After the stent is woven, the distal end of each stent is pulled to the same position, therein resulting in the rest of the interlocking joints being offset.

If there is no cover between the two layers, the two layers can be interwoven from the distal end to the proximal end.

Figure 14A:
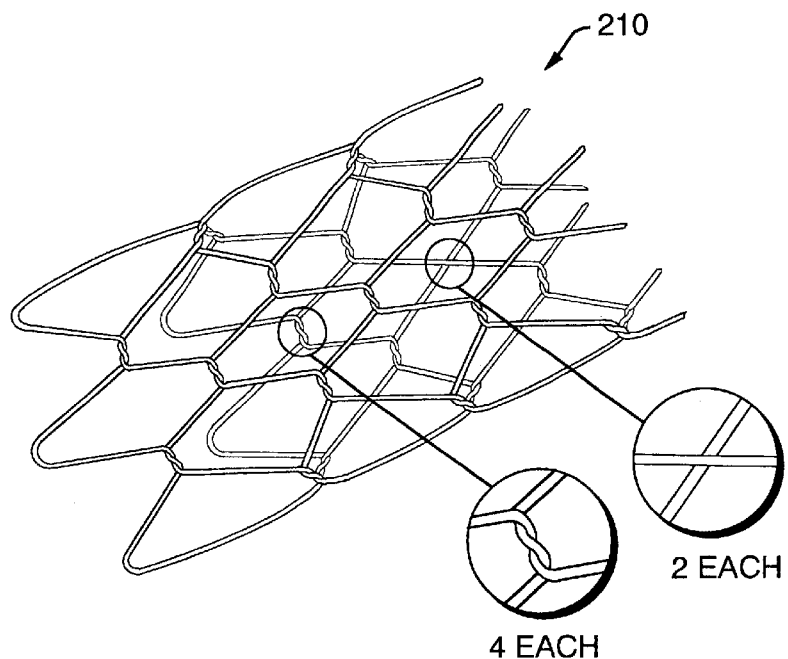
FIG. 14A is a perspective view of an alternative stent having six strands.
Figure 14B:
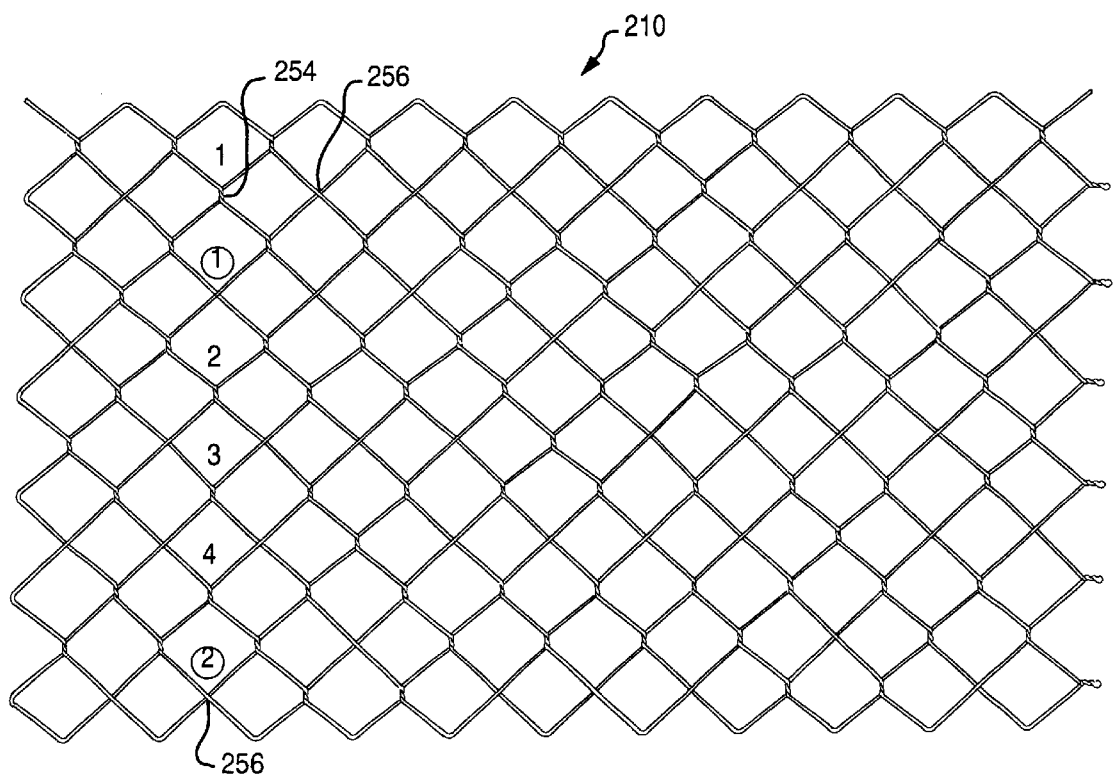
FIG. 14B is a flat layout view of the stent of FIG. 14A.

FIGS. 14A and 14B illustrate a single layer stent 210 having six strands. The stent 210 has four wrap joints 254 a pair of cross joints 256.

In one preferred embodiment, the stent 210 has a diameter of 14 millimeters in the expanded state. The stent has foreshortening in the range of 12 to 18 percent. With the strands having a diameter of 0.006 inches, the stent with only four wrap joints 254 per row can compress to fit within a 7 French system.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A medical stent comprising a first tubular body including a first plurality of strands that intersect at helically wrapped joints along the tubular body, the strands also intersecting at a plurality of crossed regions without being helically wrapped at the crossed regions, the tubular body being expandable from a constrained state to an expanded state and having a diameter of 8 French or less in the constrained state.

2. The medical stent of claim 1 wherein the helically wrapped joints extend along a circumferential direction around the stent.

3. The medical stent of claim 1 wherein a plurality of helically wrapped joints positioned along a circumference of the tubular body define a plane including at least one crossed region of a pair of strands.

4. The medical stent of claim 1 further comprising a radiopaque material formed on a region of the stent.

5. The medical stent of claim 1 wherein the stent is self-expanding from the constrained state to an expanded state in which the tubular body has a diameter in the range of 6 mm to 14 mm.

6. The medical stent of claim 1 further comprising a second tubular body positioned concentrically around the first tubular body, the second tubular body comprising a second plurality of strands.

7. The medical stent of claim 1 wherein the strands intersect to form diamond shaped cells, at least four cells extending around the circumference of the tubular body.

8. The medical stent of claim 1 wherein the tubular body has a diameter of about 2.3 mm or less in the constrained state.

9. The medical stent of claim 1 wherein each strand has a diameter in the range of 0.004 and 0.008 inches.

10. A method of delivering a stent to a site within a body lumen comprising:

providing a catheter having a distal end and a proximal end, the stent being positioned at the distal end within a moveable sheath and having a plurality of strands intersecting at helically wrapped joints and also intersecting at crossed regions at which the strands intersect without being helically wrapped, the diameter of the stent within the sheath being 8 French or less;

delivering the distal end of the catheter to a site within the body lumen; and moving the sheath to expose the stent such that the stent expands to contact a surface of the lumen.

11. The method of claim 10 wherein the step of providing a catheter further comprises providing a stent including a plurality of wrapped joints along a circumference and at least one crossed joint along the circumference.

12. The method of claim 10 wherein the step of providing a catheter further comprises providing a stent having a first tubular body within a second tubular body.

13. The method of claim 10 wherein the first tubular body comprises a plurality of strands having a first diameter and the second tubular body has a second plurality of strands and a second diameter different from the first diameter.

14. The method of claim 10 further comprising inserting the catheter through an endoscope.

15. The method of claim 10 further comprising delivering the stent to a vascular lumen, the stent of having at least two cross joints and four helically wrapped joints along a circumference of the stent.

16. A medical stent comprising a first tubular body including a first plurality of strands that intersect at helically wrapped joints along the tubular body, the strands also intersecting at a plurality of crossed regions without being helically wrapped at the crossed regions, the tubular body being expandable from a constrained state to an expanded state.

17. The medical stent of claim 16 wherein a plurality of helically wrapped joints positioned along a circumference of the tubular body define a plane including at least one crossed region of a pair of strands.

18. The medical stent of claim 16 further comprising a radiopaque material formed on a region of the stent.

19. The medical stent of claim 16 wherein the stent is self-expanding from the constrained state to an expanded state in which the tubular body has a diameter in the range of 6 mm to 14 mm.

20. The medical stent of claim 16 further comprising a second tubular body positioned concentrically around the first tubular body, the second tubular body comprising a second plurality of strands.

21. The medical stent of claim 16 wherein the strands intersect to form diamond shaped cells, at least four cells extending around the circumference of the tubular body.

22. The medical stent of claim 16 wherein the tubular body has a diameter of about 2.3 mm or less in the constrained state.

23. The medical stent of claim 16 wherein each strand has a diameter in the range of 0.004 and 0.008 inches.

* * * * *

UNITED STATES PATENT AND TRADEMARK OFFICE
CERTIFICATE OF CORRECTION

PATENT NO. : 6,264,689 B1
DATED : July 24, 2001
INVENTOR(S) : Darragh Colgan, Peter Hamilton and Paul DiCarlo It is certified that error appears in the above-identified patent and that said Letters Patent is hereby corrected as shown below:

<u>Column 10,</u>
Line 27, delete the number "10" and substitute therefor the number -- 12 --.

Signed and Sealed this

Fourteenth Day of May, 2002

Attest:

Attesting Officer

JAMES E. ROGAN
*Director of the United States Patent and Trademark Office*